United States Patent [19]

Engström

[11] Patent Number: 4,550,594
[45] Date of Patent: Nov. 5, 1985

[54] SEPARABLE COLUMN FOR CHROMATOGRAPHY WITH A DETECTION AND SIGNAL DEVICE AND AN ELUTION SYSTEM - IN COMBINATION OR SEPARATE

[75] Inventor: Nils M. L. Engström, Gothenburg, Sweden

[73] Assignees: Lars G. I. Hellgren, Vastra Frolunda; Jan G. Vincent, Stockholm, both of Sweden

[21] Appl. No.: 610,296

[22] PCT Filed: Sep. 2, 1983

[86] PCT No.: PCT/SE83/00309
§ 371 Date: May 2, 1984
§ 102(e) Date: May 2, 1984

[87] PCT Pub. No.: WO84/00900
PCT Pub. Date: Mar. 15, 1984

[30] Foreign Application Priority Data

Sep. 3, 1982 [SE] Sweden ............................. 8205033

[51] Int. Cl.4 .......................................... G01N 31/08
[52] U.S. Cl. ............................... 73/61.1 C; 210/198.2
[58] Field of Search ................. 73/61.1 C; 210/656, 210/198.2

[56] References Cited

PUBLICATIONS

Engelbrecht et al., *Dry Column Chromatography*, in Amer. Lab., vol. 9, No. 5, pp. 71-73, May 1977.
Bohen et al., *Dry Column Chromatography*, in J. Chem. Ed., vol. 50, No. 5, pp. 367-368, May 1973.

*Primary Examiner*—Stewart J. Levy
*Assistant Examiner*—Joseph W. Roskos
*Attorney, Agent, or Firm*—Cushman, Darby & Cushman

[57] ABSTRACT

Separable column for chromatography consisting of surface grinded rings (5) piled inside a tube (6) which rings tighten against each other by a tightening assembly (7, 8, 9). The rings are to be packed with a chromatography gel and after a chromatography process with movable phase they are pressed out of the tube, separated and eluted. The invention also concerns an apparatus for chromatography consisting of the column and a detection and signal device (3, 4) in order to indicate the end position of the movable phase, and possibly an elution unit adapted to each separated ring.

9 Claims, 4 Drawing Figures

SEPARABLE COLUMN FOR CHROMATOGRAPHY WITH A DETECTION AND SIGNAL DEVICE AND AN ELUTION SYSTEM - IN COMBINATION OR SEPARATE

The latest development in the field of chromatography has implied application of most sophisticated techniques in order to satisfy the demands on separation quality together with reduced process time. However, the development mainly has been dealt with the chromatography-mass in the column, together with methods allowing rapid substance/solvent passage.

Recently, a quite new type of column chromatography, a so-called "dry column chromatography" (DCC), has been introduced on the market. Examples of methods of Dry Column chromatography are described in American Laboratory, Vol. 9, No. 5, pp 71 (May 1977) and J. Chem. Educ., Vol. 5, No. 5 (May 1973), pp 367. This method allows separation of large quantities of material. Thus, when the method is applied to a DCC column, consisting of a thin-layer plastic tube, type "sausage-skin", filled with the gel material, is used. The process has inherent practical disadvantages, which makes it difficult to use, in spite of the fact that the method in itself is excellent. One of the main disadvantages is according to the manufacturers terms, the separation of ones after the chromatography procedure. This shall, according to the instructions, be done with a knife cutting through the plastic tube. Due to the fact that the plastic material is elastic, the precision is negatively influenced both by the column preparation and by its separation in zones as well after the process has been finished. Moreover, the chromatography-mass can, especially if it is partially dried, easily fall apart. Thus, the whole procedure is unsatisfactory.

Another important condition for reproducibility of the procedure is that the process always can be interrupted at a certain defined level. All previous chromatographic methods thus demand that the solvent front must be continuously supervised. Our construction has eliminated the need for visual supervision via an acoustic signal system, which in a suitable number of steps indicates the process end. Moreover, the column construction offers a direct eluting system for rapid elution of the different fractions.

SEPARABLE COLUMN

Figure 2:
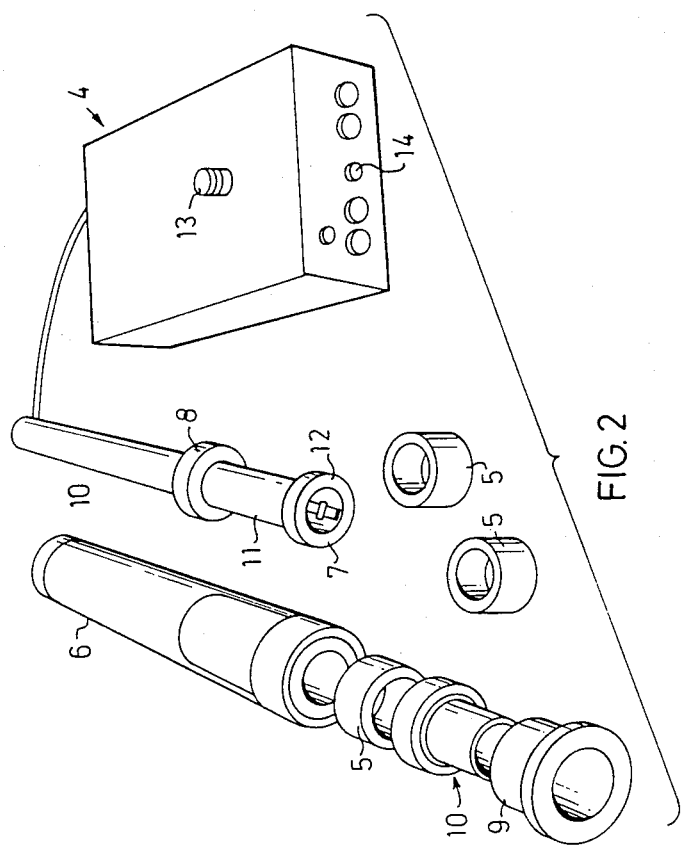
FIG. 2 shows the chromatography column in an exploded view with the various components.
Figure 1:
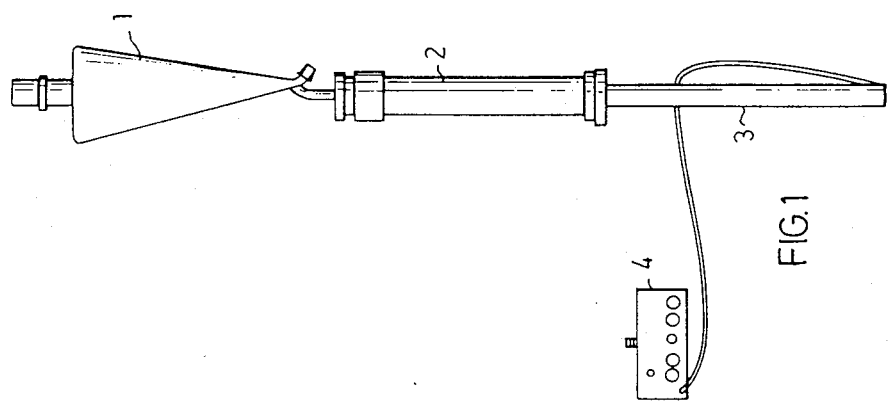
FIG. 1 shows the chromatography column assembly.
Figure 4:
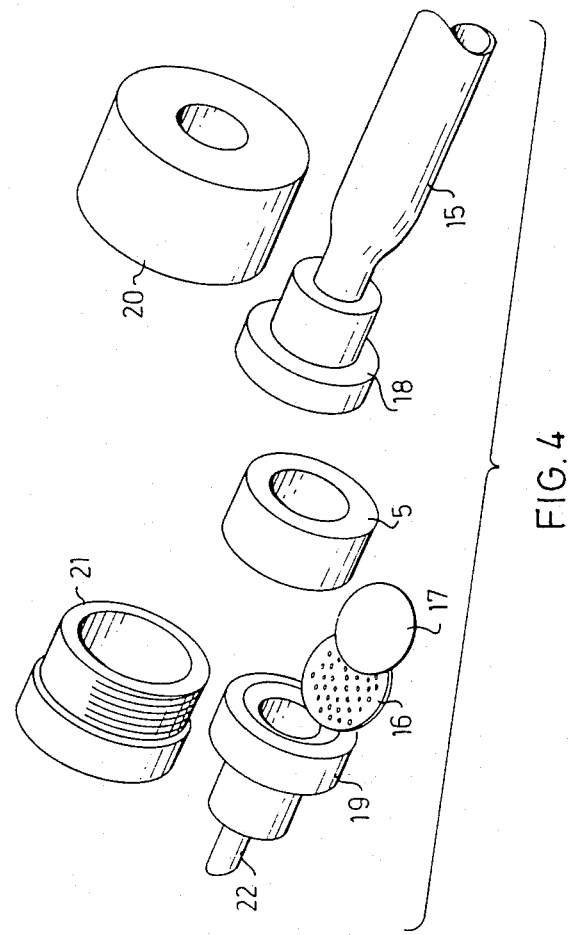
FIG. 4 shows exploded view of the segments of the chromatographic column.

The column consists of a certain number of teflon rings 5 of any dimension (also other materials can be used i.e. some form of tightening rings). Each ring 5 as shown in FIGS. 2 and 4 has two flat, turned outer surfaces, allowing leakage-free, piling or stacking to form a column 2 of any desired height. The teflon rings are piled inside an outer sheath 6 or tube of for example a plastic/metallic material threaded at both ends. The column is supported by a bottomm plate 7 and attached to the outer sheath 6 or tube by a threaded ring fastener 8. The rings are pressed together against the bottom plate by a threaded, upper ring fastener 9. The top teflon ring 10 has a guiding neck and flange, which fits the upper ring fastener.

DETECTION-AND SIGNAL ASSEMBLY

The assembly consists of a detecting element with two electrode-pairs 12 attached to the bottom plate 7 and an electronically regulated relay 4 together with an acoustic unit (buzzer or similar). The relay reacts on the increase of the electrical current, occurring between the electrodes when the solvent front moisturized the gel between them. The knob regulates a potentiometer, which is connected to a Weston bridge, by which the detection sensitivity of the electronic relay can be regulated 13. There are several other standard circuits offering the same function. As a sensor in the detection unit temperature or optoelectronics can be used. In the prototype one of the electrode-pairs is longer than the others. This allows the warning-signal to be executed in two detection levels (steps). Of course, if needed, more steps can be included.

When the gel, surrounding the upper electrode-pair, is moisturized the relay is activated and the first signal sounds. This indicates that the process is close to the end. In order to get an exact indication of the process end-point, the "level switch" 14 is manually altered to shift the detection level to the lower electrode pair so that the signal sound is off. When the signal sounds again, the exact point of the process-end is indicated; the solvent front has reached the lower electrode-pair.

ELUTION SYSTEM

Figure 3:
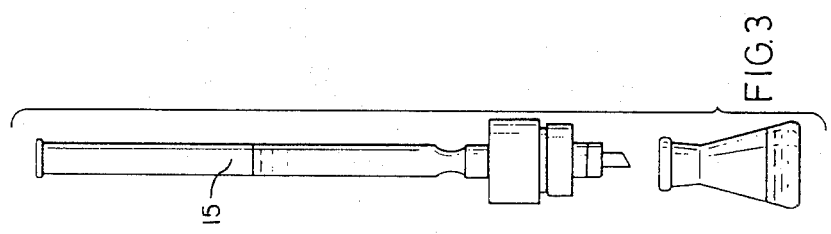
FIG. 3 shows the chromotography column in operation.

The elution system (FIG. 3) mainly consists of a number of identical units, in number the same as the teflon rings in the column. Each elution-unit consists of a house 15 dimensioned to assure sufficient space for a teflon ring containing gel to be eluted. In the bottom of the house a filter perforated disc 16 is placed on which a round filter paper 17 is placed as shown in FIG. 4. The filter tightens against the flat, ring formed surface surrounding the filter perforated disc against which the teflon ring (from the column) is pressed. Over the teflon ring a sealing ring 18 with flange and guiding neck is placed. The packing ring's neck is inside turned conically according to standard fitting on the elution column (made in glass) 5. The teflon ring of the glass column adaptor is kept in place by outer ring fasteners 20,21, which are screwed together.

The eluting column is filled with solvent, which is forced to pass only through the gel because the teflon ring (FIG. 5) is tightened by both flat surfaces. The drop-velocity is regulated by aid of outlet tap 22 built into the house.

Furthermore, the manipulation and function are described in the corresponding PCT/SE83/00309.

EXAMPLE

The separation of close fractions has been illustrated with the invention applied on DCC as shown in Experientia 37, (1981) for prostaglandins. Examples naturally can be numerous because the invention in principle can be applied on all types of chromatography.

I claim:

1. A chromatography column for dry column chromatography comprising a support tube, a plurality of ring-shaped members capable of being removably inserted into and supported by said support tube, said ring-shaped members further capable of being packed with a chromatographic gel whereby after elution the ring can be removed from the support tube to recover an eluted material.

2. A chromatography column for dry column chromatography comprising a support tube, a plurality of ring-shaped members capable of being removably received and supported by said support tube, said ring-shaped members further capable of supporting a chromatographic material, a detecting means to indicate the final stage of a chromatography process, and an elution means, the column being capable of allowing separation of said rings containing said chromatographic material.

3. A chromatography column according to claim 2 wherein the support tube includes a means to press the ring-shaped members together in a sealing engagement.

4. The chromatography column according to claim 2 wherein the support tube is threaded at both ends, each end to receive a ring fastener capable of sealingly pressing the rings together.

5. A chromatography column according to claim 4 wherein the elution system comprises a tube having a bottom provided with a perforated disc to support a filter element, said elution means connected to the support tube by said ring fasteners whereby the filter element is held in place by abutting one of said ring-shaped members.

6. A chromatography column according to claim 2 wherein the detecting means comprises a stationary sensor located on a bottom plate secured to said support tube, the stationary sensor comprising an optical-electronic sensor.

7. A chromatographic column according to claim 6 wherein the stationary sensor is a temperature sensing device.

8. A chromatographic column according to claim 6 wherein the stationary sensor is a resistance sensor.

9. A chromatography column according to claim 2 wherein a bottom plate is provided on the support tube, said bottom plate supports said detecting means, the detecting means comprising two electrode pairs and an electronically controlled relay with a signalling device, said relay controlling a rise in current when the chromatographic material is moisturized by the mobile phase.

* * * * *